US011714084B2

(12) United States Patent  
Misner et al.

(10) Patent No.: US 11,714,084 B2  
(45) Date of Patent: Aug. 1, 2023

(54) METHOD AND ASSOCIATED DEVICE FOR RAPID DETECTION OF TARGET BIOMOLECULES WITH ENHANCED SENSITIVITY

(71) Applicant: General Electric Company, Schenectady, NY (US)

(72) Inventors: Matthew Jeremiah Misner, Delanson, NY (US); Gregory Andrew Grossmann, Halfmoon, NY (US); Cathryn Ellen Olsen, Wilton, NY (US); John Richard Nelson, Clifton, NY (US); Brian Christopher Bales, Niskayuna, NY (US); David Roger Moore, Rexford, NY (US); Paul Michael Smigelski, Jr., Glenville, NY (US)

(73) Assignee: General Electric Company, Schenectady, NY (US)

( * ) Notice: Subject to any disclaimer, the term of this patent is extended or adjusted under 35 U.S.C. 154(b) by 239 days.

(21) Appl. No.: 17/090,383

(22) Filed: Nov. 5, 2020

(65) Prior Publication Data  
US 2021/0055297 A1 Feb. 25, 2021

Related U.S. Application Data

(63) Continuation of application No. 15/848,301, filed on Dec. 20, 2017, now Pat. No. 10,837,962.

(51) Int. Cl.  
*G01N 33/569* (2006.01)  
*G01N 1/40* (2006.01)  
(Continued)

(52) U.S. Cl.  
CPC ....... *G01N 33/5695* (2013.01); *B01D 15/363* (2013.01); *B01L 3/5023* (2013.01);  
(Continued)

(58) Field of Classification Search  
None  
See application file for complete search history.

(56) References Cited

U.S. PATENT DOCUMENTS 6,245,331 B1   6/2001   Laal et al.  
7,335,480 B2   2/2008   Koulchin et al.  
(Continued)

FOREIGN PATENT DOCUMENTS

| CN | 203443962 U | 2/2014 |
| WO | 9831387 A1 | 7/1998 |
| WO | 2016130638 A1 | 8/2016 |

OTHER PUBLICATIONS

Hamashur et al., "Rapid diagnosis of tuberculosis by detection of mycobacterial lipoarabinomannan in urine," Journal of Microbiological Methods, vol. 45, Issue: 1, Abstract 1 page, May 2001.  
(Continued)

*Primary Examiner* — Rebecca M Giere  
(74) *Attorney, Agent, or Firm* — Fletcher Yoder, P.C.

(57) ABSTRACT

A rapid detection method of a target biomolecule comprising an antigenic moiety is provided. The method includes providing a source biological sample comprising the target biomolecule; contacting the source biological sample to an ion-exchange medium; eluting the captured-target biomolecule from the ion-exchange medium as an eluate, and loading the eluate to a rapid diagnostic testing device comprising an antibody. The eluate comprises a concentrated form of the biomolecule in a solution having a salt concentration greater than 150 mM. A concentration of the target biomolecule in the eluate is in a range from about 2× to 25× compared to a concentration of the biomolecule in the source biological sample. The target biomolecule binds to the antibody under the salt concentration of greater than 150 mM. A device for rapid detection of target biomolecule is also provided.

18 Claims, 5 Drawing Sheets

(51) Int. Cl.
*G01N 33/543* (2006.01)
*B01L 3/00* (2006.01)
*B01D 15/36* (2006.01)

(52) U.S. Cl.
CPC ..... *G01N 1/4005* (2013.01); *G01N 33/54366* (2013.01); *B01L 2200/0631* (2013.01); *B01L 2200/10* (2013.01); *B01L 2300/0825* (2013.01); *G01N 2001/4011* (2013.01); *G01N 2333/35* (2013.01); *G01N 2405/06* (2013.01); *G01N 2469/10* (2013.01)

(56) References Cited

U.S. PATENT DOCUMENTS

| | | |
|---|---|---|
| 7,807,182 B2 | 10/2010 | Laal et al. |
| 9,512,206 B2 | 12/2016 | Katsuragi et al. |
| 2007/0244368 A1 | 10/2007 | Bayloff et al. |
| 2011/0097318 A1* | 4/2011 | Gadgil ............ A61M 5/2448 141/2 |
| 2014/0377770 A1 | 12/2014 | Bischof et al. |

OTHER PUBLICATIONS

Hunter et al., "Structure and Antigenicity of the Phosphorylated Lipopolysaccharide Antigens from the Leprosy and Tubercle Bacilli," The Journal of Biological Chemistry, vol. 261, No. 26, Issue of Sep. 15, pp. 12345-12351, 1986 (Year: 1986).

Minion et al., "Diagnosing tuberculosis with urine lipoarabinomannan: systematic review and meta-analysis," European Respiratory Journal, vol. 38, Issue: 6, pp. 1398-1405, Dec. 2011.

Sada et al., "Evaluation of Lipoarabinomannan for the Serological Diagnosis of Tuberculosis," Journal of Clinical Microbiology, Dec. 1990, pp. 257-2590. (Year: 1990).

"Optimize elution conditions for immunoaffinity purification," Tech Tip #27, Thermo Scientific, TR0027.1, Thermo Fisher Scientific Inc. 2009, 2 pgs.

* cited by examiner

METHOD AND ASSOCIATED DEVICE FOR RAPID DETECTION OF TARGET BIOMOLECULES WITH ENHANCED SENSITIVITY

CROSS-REFERENCE TO RELATED APPLICATIONS

The present application is a continuation of U.S. patent application Ser. No. 15/848,301, filed on Dec. 20, 2017, which is hereby incorporated by reference in its entirety herein for all purposes.

This application relates generally to a rapid detection method of infectious disease. In a particular aspect, the application relates to a rapid detection method and an associated device for rapid diagnostic testing of a target biomolecule.

BACKGROUND

A rapid detection method of analytes or target biomolecules performed by employing a rapid diagnostic test (RDT) is relatively less time consuming and less labor intensive as compared to conventional methods. Rapid diagnostic tests (RDTs) have been used for detection of various infectious diseases. The RDTs are suitable for preliminary and/or emergency medical screening, for example, for use in medical facilities with limited resources, and offer a useful alternative to microscopy in situations where reliable microscopic diagnosis facility is not available or is not immediately available. RDTs also allow point of care (POC) testing in primary care. RDTs can be performed independent of laboratory equipment by minimally trained personnel, and are adapted to deliver instant results. RDTs provide results within 2 hours to 10 minutes. An RDT employs a dipstick or cassette format for testing a biological specimen, such as a urine sample. For testing, the biological specimen collected from a patient is applied to a sample pad on a test strip (or card) of the RDT dipstick or cassette along with certain reagents. Depending on the type of test that is being conducted, after a determined period of time, presence or absence of specific bands in a test strip window indicates whether a certain antigen of interest is present in the biological specimen, such as a patient's sample. Generally, a drop of the biological specimen is added to the RDT device through a sample well, and then a buffer is usually added through a buffer well. The buffer carries the biological specimen along the length of the RDT device.

Among major infectious diseases, tuberculosis is different in that it lacks accurate rapid point-of-care diagnostic tests. Inefficient detection methods and lack of timely treatment of tuberculosis are major causes of failure to control the spread of tuberculosis. Laboratory based diagnostic tests for detecting tuberculosis are currently available, however these tests need multiple investigations over a period of weeks or months. Multiple new diagnostic tests have recently been developed for detecting active tuberculosis, latent tuberculosis infection, and identifying drug-resistant strains of Mycobacterial tuberculosis. However, a robust point-of-care test with high accuracy, greater accessibility, reduced cost and complexity is desirable for early detection of tuberculosis. Further, an effective method for diagnosing extrapulmonary mycobacterial tuberculosis infections, which are on the rise in HIV-positive subjects, is also highly desirable.

Prior methods for detecting surface polysaccharides (LAM) using different body fluids, such as serum, urine or sputum, have been investigated, but have proven ineffective. For example, prior studies with urine sample required extensive sample processing and manipulation, rendering such methodologies complex and cumbersome, specifically in the field.

BRIEF DESCRIPTION

In some embodiments, a rapid detection method of a biomolecule is provided. The method comprises providing a source biological sample comprising the biomolecule; contacting the source biological sample to an ion-exchange medium comprising one or more ligands to capture the biomolecule and form a captured-biomolecule; eluting the captured-biomolecule from the ion-exchange medium as an eluate, and loading the eluate to a rapid diagnostic testing device comprising an antibody. The biomolecule comprises an antigenic moiety. The eluate comprises a concentrated form of the biomolecule in a solution. A concentration of the biomolecule in the eluate is in a range from about 2× to 25× compared to a concentration of the biomolecule in the source biological sample. The solution has a salt concentration greater than 150 mM. The biomolecule binds to the antibody under the salt concentration of greater than 150 mM.

In some other embodiments, a method for rapid diagnostic testing of a source urine sample comprising tuberculosis-lipoarabinomannan (TB-LAM) is provided. The method comprises (a) concentrating the TB-LAM by: diluting the source urine sample by at least 2× compared to the source urine sample to form a diluted urine sample; contacting the diluted urine sample to an anion-exchange medium to capture the TB-LAM of the diluted urine sample; capturing the TB-LAM of the diluted urine sample by the anion-exchange medium; and eluting the captured-TB-LAM from the anion-exchange medium as a concentrated form of TB-LAM in an eluate under a salt concentration of at least 1M. A concentration of the TB-LAM in the eluate is in a range from about 2× to 25× compared to a concentration of the TB-LAM in the diluted urine sample. The method also comprises (b) loading the eluate comprising the concentrated form of the TB-LAM of step (a) to a lateral flow assay device comprising a TB-LAM-specific antibody for binding the concentrated form of the TB-LAM. The eluate is loaded without any dilution, and wherein the TB-LAM binds to the TB-LAM-specific antibody under the salt concentration of at least 1M.

Another embodiment of a device is also provided. The device comprises a) a concentrator unit comprising an anion exchange medium to concentrate an antigen from a biological sample and generate a concentrated form of the antigen; and b) an immune-based assay unit comprising an antibody to bind the concentrated form of the antigen received from the concentrator unit, wherein the concentrator unit is operatively coupled to the immune-based assay unit to allow loading of the concentrated form of the antigen from the concentrator unit to the immune-based assay unit.

DRAWINGS

These and other features, aspects, and advantages of the present invention will become better understood when the following detailed description is read with reference to the accompanying drawings in which like characters represent like parts throughout the drawings, wherein:

FIG. 4 is an image depicting different commercially available rapid diagnostic test strips showing presence of TB-LAM in a flow through.

DETAILED DESCRIPTION

A rapid detection method and associated devices are provided, which overcome difficulties in the currently known methods or devices by providing enriched target biomolecules (e.g., mycobacterial antigens) in a biological sample collected from a subject. The biological sample enriched with target biomolecule further enhances sensitivity of the rapid diagnostic tests. In accordance with certain embodiments, a rapid detection method of target biomolecules present in a biological sample employs rapid diagnostic tests (RDTs) or rapid diagnostic test (RDT) devices. Rapid diagnostic testing devices produce a visible band on a rapid diagnostic testing device by capturing a target biomolecule (antigens) using antibodies, such as dye-labeled antibodies. For rapid diagnostic testing, in one aspect, the dye-labeled antibody or conjugate particle-coupled antibody binds to the target biomolecule (antigen), such as a tuberculosis biomarker. The resultant target biomolecule-antibody complex may further be captured by a secondary antibody or a conjugate particle-coupled secondary antibody forming a visible band (test line) in a result window of the rapid diagnostic testing device.

To more clearly and concisely describe the subject matter of the disclosed application, the following definitions are provided for specific terms, which are used in the following description and the appended embodiments. Throughout the specification, exemplification of specific terms should be considered as non-limiting examples.

The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "rapid diagnostic test" or RDT refers to a device or a test of a biological sample, which can be carried out at the point of care to obtain fast diagnosis. Rapid diagnostic testing devices or rapid diagnostic testing devices employ rapid diagnostic tests that are medical diagnostic tests that are quick and easy to perform and can be carried out even in the absence of laboratory techniques such as microscopy, enzyme-linked immunosorbent assay (ELISA) or polymerase chain reaction (PCR). By way of a non-limiting example, rapid diagnostic testing for tuberculosis typically require about 30 minutes from the time of sample collection to the time of obtaining a result. It should be noted that time required for a rapid diagnostic testing depends on variables, such as the type of sample, the amount of sample, the nature of the analyte, and the like.

Embodiments of a rapid detection method of a target biomolecule using a rapid diagnostic testing device are presented herein. The rapid detection method and the rapid diagnostic testing device are compatible with equipment-free, point of care analyte-separation and detection process. For example, the rapid diagnostic testing device provides rapid diagnostic testing by immunochromatographic separation and detection of biomolecule from a biological sample, such as urine. Improved sensitivity of a rapid diagnostic testing is desired, however, an early detection of tuberculosis (TB) is made complicated by frequent false positive tests and a huge variability of band intensity particularly in the very low concentration range.

According to embodiments of the present technique, a rapid detection method of a target biomolecule comprises providing a source biological sample comprising the target biomolecule, contacting the source biological sample to an ion-exchange medium and form a captured-target biomolecule, eluting the captured-target biomolecule from the ion-exchange medium as an eluate comprising a concentrated form of the target biomolecule in a solution, and loading the eluate to an rapid diagnostic testing device comprising an antibody. The target biomolecule of the source biological sample comprises an antigenic moiety. The ion-exchange medium comprises one or more ligands to capture the target biomolecule. A concentration of the target biomolecule in the eluate is in a range from about 2× to 25× compared to a concentration of the target biomolecule in the source biological sample. The eluate comprises the concentrated form of the target biomolecule in the solution, where the solution has a salt concentration greater than 150 mM. The target biomolecule binds to the antibody of the rapid diagnostic testing device under the salt concentration of greater than 150 mM.

In one or more embodiments, the target biomolecule is a glycolipid. The target biomolecule may comprise a lipoarabinomannan (LAM), which is a complex lipopolysaccharide antigen composed of mannose and arabinose residues forming a highly branched and complex structure. In some embodiments, the target biomolecule is a tuberculosis-lipoarabinomannan (TB-LAM). In such embodiments, if the TB-LAM is detected in the biological sample (such as urine), it is concluded that the biological sample is collected from a TB-positive subject. LAM is a virulence factor associated with *Mycobacterium tuberculosis*, the bacteria responsible for TB. The bacterium survives in the human reservoir by undermining host resistance and acquired immune responses by inhibiting T-cell proliferation and macrophage microbicidal activity. It is believed that as LAM outflows into the circulation in an active TB infection and passes through the kidneys, LAM can be detected in the urine sample of a TB patient reflecting the level of mycobacterial burden. TB-LAM is typically found in human urine at very low concentration, such as in picogram level. The RDTs are prone to give false positive results to identify TB-LAM at such low concentration levels. To achieve desired results using RDTs, a concentrated form of TB-LAM may be used.

Figure 1:
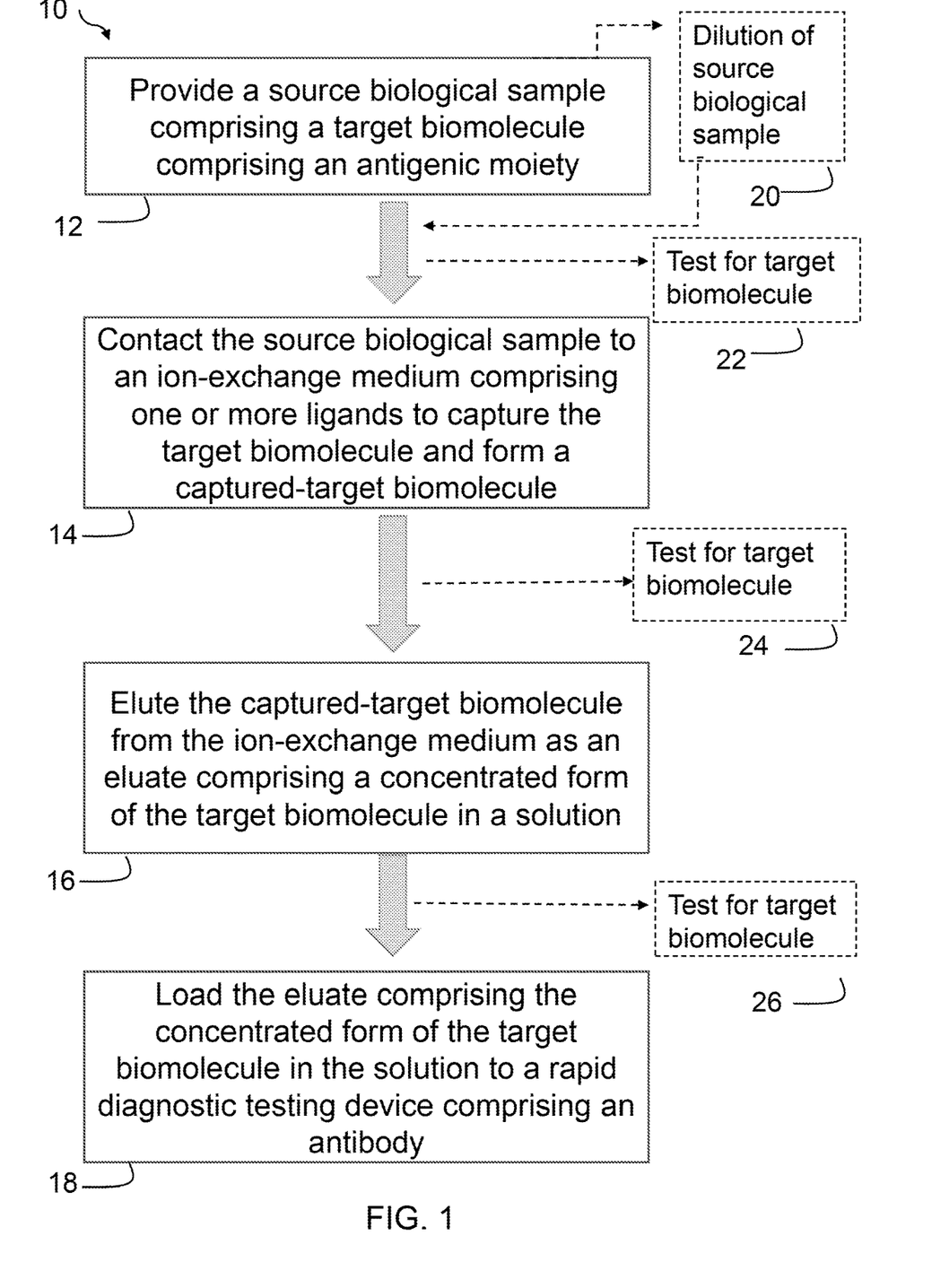
FIG. 1 is a flow chart illustrating one embodiment of a rapid detection method of a biomolecule.

Referring now to FIG. 1, a method 10 for r medium is effected under a salt concentration in a range from about 0.75M to about 1.75M. In certain embodiments, the elution of the captured-biomolecule from the ion-exchange medium is effected under a salt concentration in a range from about 1M to about 1.5M. As such, the eluate, which is directly loaded to the rapid diagnostic testing device, comprises a concentrated form of the biomolecule (TB-LAM) in a buffer of high salt concentration.

As noted, at block 18, the eluate comprising the concentrated form of the target biomolecule in the solution is loaded to a rapid diagnostic testing device, wherein the rapid diagnostic testing (RDT) broadly includes enzyme linked immuno-sorbent assay (ELISA), lateral flow assays (LFAs), and/or flow through assays (FTAs). In one embodiment, the rapid diagnostic testing employed for the method of rapid detection of target biomolecule is a lateral flow assay (LFA). Sensitivity of the immunochromatographic antigen-detection tests further rely on binding efficiency of an antigen (here, target biomolecule, such as TB-LAM) to an antibody and the stability of the antigen-antibody complex. To provide a better binding efficiency of a target biomolecule to an antibody, a concentrated form of the target biomolecule (such as TB-LAM) present in the eluate is directly loaded to the rapid diagnostic testing device comprising an antibody to form a stable target biomolecule-antibody complex. In some embodiments, the eluate is collected using a buffer solution having a salt concentration greater than 150 mM in a volume of 70-100μ and directly loaded to the rapid diagnostic testing device, without any dilution. A small volume of eluate, such as 70-100μ, comprising the concentrated form of the target biomolecule in a buffer of high salt concentration may be loaded to the rapid diagnostic testing device comprising an antibody. In some cases, 50-100 μL of eluate comprising the concentrated form of the biomolecule in a buffer of high salt concentration may also be loaded to the RDT device comprising an antibody. In some other embodiments, the eluate may be diluted before loading the eluate to the rapid diagnostic testing device, however the dilution is maintained such that it does not affect the binding efficiency of the antigen and antibody, as well as the stability of the antigen-antibody complex.

With respect to block 18, for rapid detection of a target biomolecule, the efficient binding of the target biomolecule-antibody occurs under a salt concentration greater than 150 mM, which is an unexpected result. In some embodiments, the target biomolecule binds to the antibody under a salt concentration in a range from about 0.5M to about 2M. In some other embodiments, the target biomolecule binds to the antibody under a salt concentration of about 1.3M. The binding of an antigen (target biomolecule) to an antibody under such salt concentration (greater than 150 mM) is not reasonably expected considering standard protocol of immunoprecipitation. Generally, a salt concentration of greater than 150 mM is the range where standard antigen-antibody binding assays are not expected to be successful. As the antibodies are designed to bind to a target antigen inside a body of a living subject under a physiological condition of salt concentration, such as less than 150 mM salt, the salt concentration of less than 150 mM is selected for standard protocol of immunoprecipitation for successful antigen-antibody binding assay. The art recognized buffers for complete elution of antibodies from the antigen-antibody complexes include 100 mM Glycine, pH2.5 (acidic pH), 1M Triethanolamine; TEA (basic pH), 4M $MgCl_2$ (high salt), 1M NaCl/PBS (high salt). A salt concentration of 1M is currently used to completely detach an antibody from an antigen-antibody complex. Considering these facts, an antigen-antibody interaction on the rapid diagnostic testing device under such salt concentration of greater than 150 mM is quite unexpected. The Examples 1-3, FIGS. 5-7 also demonstrate the desired antigen-antibody interaction under a salt concentration in a range from about 0.5M to about 2M. In one example, the biomolecule, such as TB-LAM (antigen) binds to the antibody under the salt concentration of 1.3M (Examples 1-3, FIGS. 5-7), which is an unexpected result.

The target biomolecule binds to the antibody on a rapid diagnostic testing device, wherein the rapid diagnostic testing method comprises generating a signal on antigen-antibody binding. For example, on binding of the TB-LAM to the TB-LAM-specific antibody, such as reporter-linked TB-LAM specific antibody, a signal is generated in case of exceeding a pre-determined threshold value for a concentration of the TB-LAM. The higher signal intensity is advantageous for detection of target biomolecule because generally RDTs rely on visually detected changes in color of the test region on an immune-based assay unit. A faint color change is not visually detectable and could lead to a false negative result on the RDT device. The method 10 ensures generating a concentrated form of target biomolecule, such as TB-LAM and loading the concentrated form of the target biomolecule TB-LAM to the RDT device comprising TB-LAM-specific antibody to generate better signal intensity compared to the commercially available RDTs. The method 10 is also effective for diagnosing extra-pulmonary mycobacterial infections for a subject having co-infection of TB and human immune deficiency virus (HIV).

In certain embodiments, the rapid detection method described herein may be used to detect tuberculosis-lipoarabinomannan (TB-LAM) in a urine sample. The method comprises (a) concentrating the TB-LAM by: diluting the source urine sample by at least 2× compared to the source urine sample to form a diluted urine sample; contacting the diluted urine sample to an anion-exchange medium to capture the TB-LAM of the diluted urine sample; capturing the TB-LAM of the diluted urine sample by the anion-exchange medium; and eluting the captured-TB-LAM from the anion-exchange medium as a concentrated form of TB-LAM in an eluate under a salt concentration of at least 1M. A concentration of the TB-LAM in the eluate is in a range from about 2× to 25× compared to a concentration of the TB-LAM in the diluted urine sample. The method also comprises (b) loading the eluate comprising the concentrated form of the TB-LAM of step (a) to a lateral flow assay device comprising a TB-LAM-specific antibody for binding the concentrated form of the TB-LAM. The eluate is loaded without any dilution, and wherein the TB-LAM binds to the TB-LAM-specific antibody under the salt concentration of at least 1M.

In certain embodiments, the device structure is described herein to generally correlate the method steps to the device components. A device for rapid detection of a target biomolecule from a source biological sample is provided. The device comprises a) a concentrator unit comprising an anion exchange medium to concentrate an antigen from a biological sample and generate a concentrated form of the antigen; and b) an immune-based assay unit comprising an antibody to bind the concentrated form of the antigen received from the concentrator unit, wherein the concentrator unit is operatively disposed on the immune-based assay unit to allow loading of the concentrated form of the antigen from the concentrator unit to the immune-based assay unit. In some embodiments, the antigen is TB-LAM. The immune-based assay unit comprises one or more rapid diagnostic testing device, enzyme linked immune sorbent assay (ELISA), lateral flow assay, or a combination thereof. In some embodiments, the device further comprises a dilutor unit.

Figure 2A:
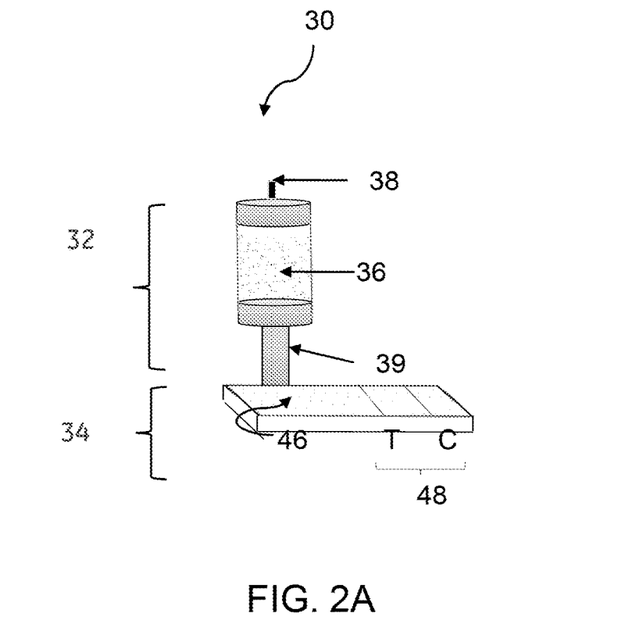
FIG. 2A is a schematic drawing of a perspective view of one embodiment of a device for rapid detection of a biomolecule.

Referring to FIG. 2A, a device 30, in accordance with one embodiment, comprises a concentrator unit 32 and an immune-based assay unit 34. The concentrator unit 32 comprises an anion exchange medium 36 to concentrate a target biomolecule (an antigen) present in a source biological sample and generate a concentrated form of the target biomolecule. The immune-based assay unit 34 comprises an antibody to bind the concentrated form of the target biomolecule (such as antigen) received from the concentrator unit 32. The concentrator unit 32 is operatively coupled to the immune-based assay unit 34 to allow loading of the concentrated form of the target biomolecule, such as antigen from the concentrator unit 32 to the immune-based assay unit 34. The concentrator unit 32 of the device 30 also includes an input channel or inlet 38 for loading the source biological sample to the ion-exchange medium 36. The concentrator unit 32 further includes an output channel or outlet 39 for allowing the eluate to flow from the concentrator unit 32 to the immune-based assay unit 34. The eluate comprises a concentrated form of the target biomolecule. In some other embodiments of FIG. 2A, the source biological sample may be introduced in the device 30 without any dilution. In these embodiments, the source biological sample is contacted with the ion-exchange medium 36 without any dilution. In such embodiments of device 30, a salt-tolerant anion-exchange medium, for example, an anion exchange membrane containing primary amine may be used.

Figure 6:
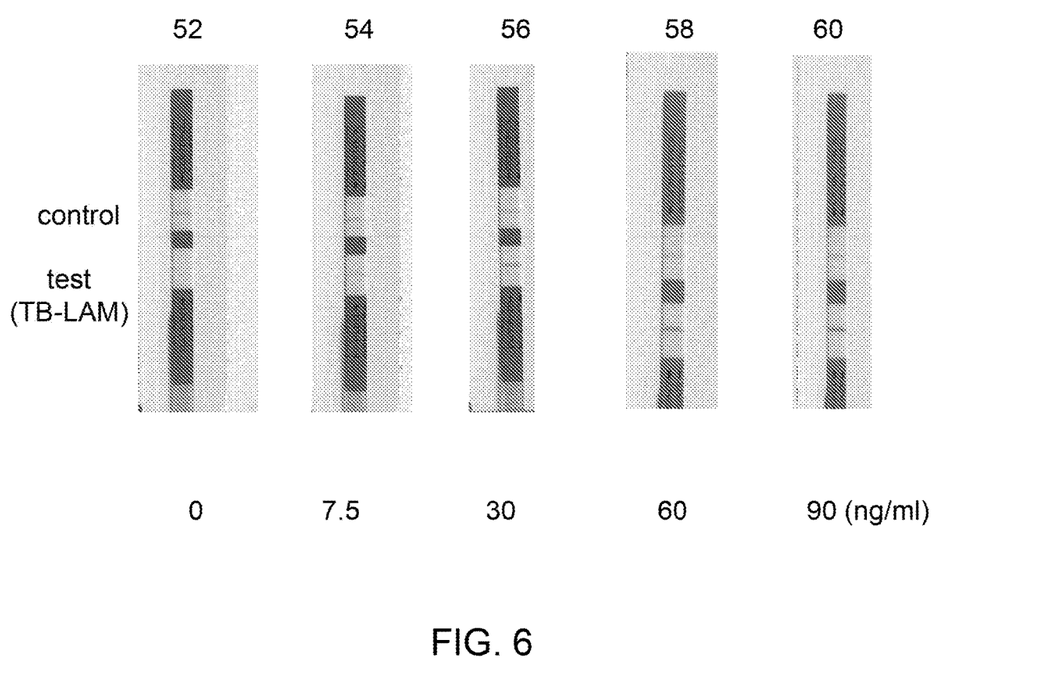
FIG. 6 is an image illustrating different rapid diagnostic test strips showing concentrated (15×) form of TB-LAM in different eluate samples compared to a control with no TB-LAM.
Figure 7:
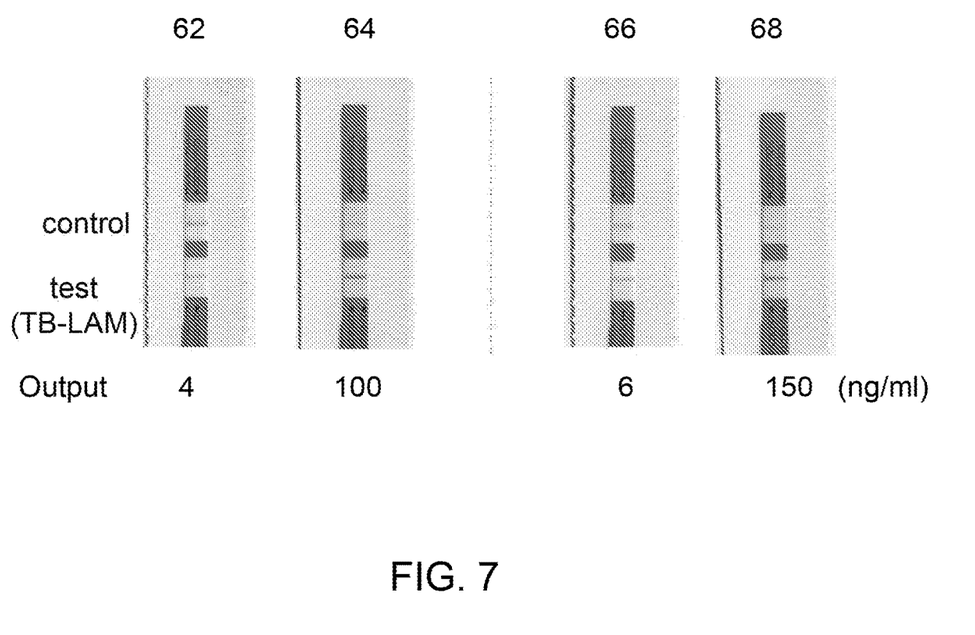
FIG. 7 is an image illustrating different LFA test strips showing concentrated (25×) form of TB-LAM in different eluate samples eluted from the ion-exchange medium as compared to control samples which are not contacted with the ion-exchange medium.

In some embodiments, the ion-exchange medium 36 is disposed in the concentrator unit 32 for rapid separation of the undesired constituents from the biological sample and at least generates a concentrated form of the target biomolecules. By using the ion-exchange medium 36, a concentration of the target biomolecule in the eluate may be increased to 2× to 25× compared to a concentration of the target biomolecule in the source biological sample. For example, by using a Q+ anion exchange membrane for concentrating the target biomolecule, the TB-LAM is concentrated by 15× and 25×, as shown in FIGS. 6 and 7, respectively, as will be described later.

The ion-exchange medium 36 comprises one or more ligands, wherein the ligands comprise cationic- or anionic-exchange ligands. The anionic-exchange ligands include, but are not limited to, quaternary ammonium ion, and dimethyl aminoethyl (DMAE) groups.

In some embodiments, the ion-exchange medium 36 includes an ion exchange material, an ion-exchange membrane, or an ion-exchange matrix. The ion-exchange medium 36 may be disposed on the concentrator unit 32 for concentrating the target biomolecule. In one embodiment, the ion-exchange medium is an anion-exchange membrane, for example Q+ membrane (GE Healthcare Life Sciences, Pittsburgh, Pa., US). Further, the anion exchange membrane is easily adaptable to the concentrator unit and to the immune-based assay unit, such as RDT. The anion exchange membrane is also easy to dispose to the concentrator unit 32 in the field-able applications. In some embodiments, an anion-exchange membrane specific for capturing TB-LAM may be used to concentrate TB-LAM before loading the eluate comprising the concentrated form of the TB-LAM to the rapid diagnostic testing device. For example, an amine-based ion-exchange membrane is employed to concentrate TB-LAM from the urine sample. In such embodiments, the amine-based ion-exchange membrane is used for concentrating TB-LAM, which significantly improves a signal for detection of TB.

In an alternate embodiment, the ion exchange medium 36 may comprise an anion-exchange resin. In such embodiment, a column chromatography containing an anion exchange resin is used to capture and concentrate the target biomolecule, such as TB-LAM. For example, Capto™Adhere resin (GE Healthcare Life Sciences, Pittsburgh, Pa., US) or Capto™Adhere ImpRes resin (GE Healthcare Life Sciences, Pittsburgh, Pa., US) may be selected as the anion-exchange resin to capture TB-LAM. In the anion-exchange resin chromatography, a larger volume of buffer is required to elute the biomolecule compared to the volume of buffer required for anion-exchange membrane. Further, an efficient packing of the resin and refrigeration of the resin are required in the anion exchange resin chromatography.

Figure 2B:
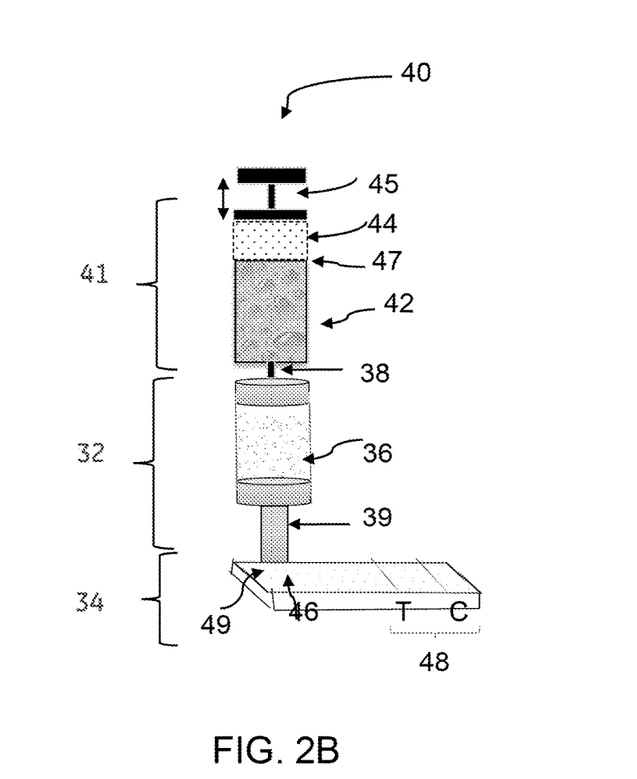
FIG. 2B is a schematic drawing of a perspective view of another embodiment of a device for rapid detection of a biomolecule.

Referring now to FIG. 2B, a device 40 comprises a dilutor unit 41 in addition to the components of the concentrator unit 32, and the immune-based assay unit 34 of FIG. 2A. The device 40 may be employed in embodiments where it is desirable to dilute the source biological sample in the device 40 before contacting the source biological sample with the ion exchange medium 36. The dilutor unit 41 includes a dilutor 42 and an input chamber 44. The input chamber 44 is configured to receive the source biological sample. The dilutor unit 41 is coupled to the concentrator unit 32, and operatively coupled to the immune-based assay unit 34 via the concentrator unit 32. The dilutor 42 may be a mixing chamber or mixing vessel where the dilution of the source biological sample takes place by mixing the source biological sample with an appropriate buffer solution. In some embodiments, the dilutor 42 may be pre-filled with a buffer solution as per requirement of the desired dilution. In some embodiments, the required volume of buffer is added to the dilutor 42 after addition of the source biological sample to the input chamber. The input chamber 44 is a chamber for receiving the source biological sample and feeding the source biological sample to the dilutor 42 in a controlled manner using a plunger 45. In some embodiments, the input chamber 44 is a syringe having a plunger. The plunger 45 may be linearly pulled and pushed along the inside of the chamber 44 in directions represented by arrows 49, allowing the chamber 44 (e.g., syringe) to receive and discharge the source biological sample through a discharge outlet 47 located at the front end (opposite end of the plunger 45) of the input chamber 44 such as the syringe. The discharge outlet 47 may be an orifice, a membrane, or a filter through which the source biological sample may pass through and enter the dilutor 42.

Referring now to both FIGS. 2A and 2B, the concentrator unit 32 receives at least a portion of the diluted biological sample through the inlet 38. The concentrator unit 32 comprises an ion-exchange medium 36 for rapid separation of undesired materials from the source biological sample and forms at least partially purified biological sample comprising concentrated form of the biomolecule. The eluate comprising the concentrated form of the target biomolecule is directed to the immune-based assay unit 34 through an outlet 39 of the concentrator unit 32.

In some embodiments, the immune-based assay unit 34 is a lateral flow unit. The lateral flow unit comprises a sample receiving zone 46 and a detection zone 48. The sample receiving zone 46 may further be referred to as a "sample application pad" or a "sample pad." The sample receiving zone 46 is operatively coupled to the concentrator unit 32 such that the concentrated form of the biomolecule, such as TB-LAM is received from the concentrator unit 32 by the sample receiving zone 46. The sample receiving zone 46 may be present on a fiber glass, quartz, or a cellulose substrate for receiving the biological sample comprising a concentrated form of the target biomolecule.

Optionally, a conjugate zone 49 is disposed adjacent to and upstream of the sample receiving zone 46, wherein the conjugate zone comprises a conjugate particle for binding with the target biomolecule. The detection zone 48 is disposed adjacent to and downstream of the sample receiving zone 46. The detection zone 48 comprises at least one antibody for capturing the target biomolecule.

As noted, the concentrator unit 32 is operatively coupled to the immune-based assay unit 34, such as a LFA unit, to allow loading of the concentrated form of the antigen from the concentrator unit 32 to the immune-based assay unit 34. The concentrator unit 32 and the lateral flow unit 34 are operatively coupled or connected at least by a fluidic communication. The fluidic communication facilitates a fluid flow from the concentrator unit 32 to the immune-based assay unit 34 such as a lateral flow unit during operation of the device 30, 40. For example, a urine sample flows from the concentrator unit 32 to the lateral flow unit 34, which provides a fluidic communication under the operating conditions of the diagnostic testing device. In some embodiments, the concentrator unit 32 and the immune-based assay unit 34 may be in physical contact with one another. In such embodiments, the concentrator unit 32 and the immune-based assay unit 34 may be coupled or connected by a mechanical fastener.

In certain embodiments, the concentrator unit 32 of the device 30 or 40 and the immune-based assay unit 34 are disposed at angles in a range from 30 degrees to 120 degrees with respect to one another. In some embodiments, the concentrator unit 32 and the immune-based assay unit 34 are vertically disposed with respect to one another. In particular, in these embodiments, planes of the concentrator unit 32 and the immune-based assay unit 34 are disposed at 90-degree angle with respect to one another.

As noted, immune-based assay unit, such as a rapid diagnostic testing device 34 comprises an antibody, wherein the antibody is specific to the antigenic moiety of the target biomolecule. For example, the rapid diagnostic testing device comprises a TB-LAM-specific antibody. In one or more embodiments, the antibody is a monoclonal antibody. In some other embodiments, the antibody is a polyclonal antibody. In some examples, the polyclonal antibody is an affinity purified polyclonal antibody. Due to high structural complexity and variability of TB-LAM, a complex spectrum of antigenic epitopes is generated. The use of affinity purified polyclonal antibody allows to cover the full spectrum of antigenic specificities potentially associated with LAM present in clinical samples. To achieve the desired assay sensitivity of immunoassay, for example in a sandwich immunoassay, the highest concentration of antigen-specific labeled antibody may be used. The enriched antibodies may be raised to the antigenic moiety of the TB-LAM, may be for a specific epitope of LAM in an environment which maintains its antigenic activity.

In one or more embodiments, the TB-LAM-specific antibody used for a RDT device, such as immune-based assay unit 34 (e.g., LFA strip), is a reporter-linked TB-LAM-specific antibody or a labeled antibody. As used herein, "labeled antibody" includes an antibody coupled to an enzyme or a substrate. In some examples, the enzyme is capable of changing color on exposure to a substrate. In some examples, the substrate is capable of changing color on exposure to a reagent (such as an enzyme), respectively. As such, the antibody may be labeled with a dye, a metal particle (e.g., gold), a compound capable of producing chemiluminescence or fluorescence. In alternative embodiments, the antibody may be attached to a magnetic bead, a cellulose bead, a polymeric bead labeled with a dye, an affinity probe, and the like.

In some embodiments, the immune-based assay unit 34 of the device 30 or 40 is a lateral flow assay (LFA) unit, an enzyme linked immuno-sorbent assay (ELISA) unit, or a combination thereof. In one embodiment, the immune-based assay unit 34 is a LFA unit, wherein the LFAs are used for detection of target biomolecules, such as different biomarkers present in a source biological sample (such as urine). In some embodiments, the LFA includes dye-labeled antibodies to capture biomolecules and produce a visible band on the LFA unit, such as a nitrocellulose test strip. In certain embodiments, the target biomolecule (such as TB-LAM) binds to the antibodies disposed on the test line forming biomolecule-antibody complexes, which are further bound to conjugate particle-coupled antibodies on the test line, forming a visible test line in the result window. In immune-based assay unit 34, the antibodies are attached to another line, a second line, referred to herein as a control line (referred to as "C"). This control line typically comprises a species-specific anti-immunoglobulin antibody, specific for the conjugate particle-coupled antibody. The control line gives information on integrity of the conjugate particle-coupled antibody and fluidics of the lateral flow unit.

As illustrated in FIGS. 2A and 2B, a concentrated form of the target biomolecule, such as TB-LAM is received by the sample receiving zone 46. The detection zone 48 comprises at least one binding agent for detecting the at least one biomolecule by capturing the biomolecule. The detection zone may be constructed on a nitrocellulose membrane. In one embodiment, the detection zone may be formed by depositing one or more binding agents on the nitrocellulose membrane. The detection zone 48 comprises a test region or test line "T." The test region is a sub-zone of the detection zone 48 where antibody is deposited. The detection zone further comprises a control region or control line "C." One or more binding agents having affinity towards the conjugate particles deposit on the control region C, these binding agents do not exhibit any affinity towards the biomolecule. The target biomolecule (such as TB-LAM) binds to the antibodies disposed on the test line T forming biomolecule-antibody complexes. The biomolecule-antibody complex may further bound to conjugate particle-coupled antibodies on the test line T, forming a visible test line in the result window (not shown in FIGS. 2A and 2B). The presence of the target biomolecule is visually detected by change in color of the test region T in the detection zone 48 on a lateral flow unit. In immune-based assay unit, such as a LFA unit, the antibodies are attached to a different line other than the test line T, referred to herein as a control line C at the detection zone 48. The control line C gives information on integrity of the conjugate particle-coupled antibody and fluidics of the lateral flow unit, as the control line C typically comprises a secondary antibody specific for the conjugate particle-coupled antibody.

The conjugate particle may include colloidal gold, a colored particle, a fluorescent probe, a paramagnetic particle (such as paramagnetic monodisperse latex particle), or combinations thereof. The lateral flow unit 34 may further include alternative conjugate reporters such as cellulose nanobeads (CNB), magnetic beads, fluorescence tags, chemiluminescence molecules, or various shapes of gold nanoparticles including nanospheres, nanorods, and nanoshells. Such alternative conjugate reporters are contemplated within the scope of embodiments presented herein. The conjugate particle is conjugated to one of the components of the biological sample, a component of the lateral flow assay strip (such as binding agent), or a biomolecule such as a protein. The protein may be an antigen or an antibody, depending on a format of the assay.

Figure 3:
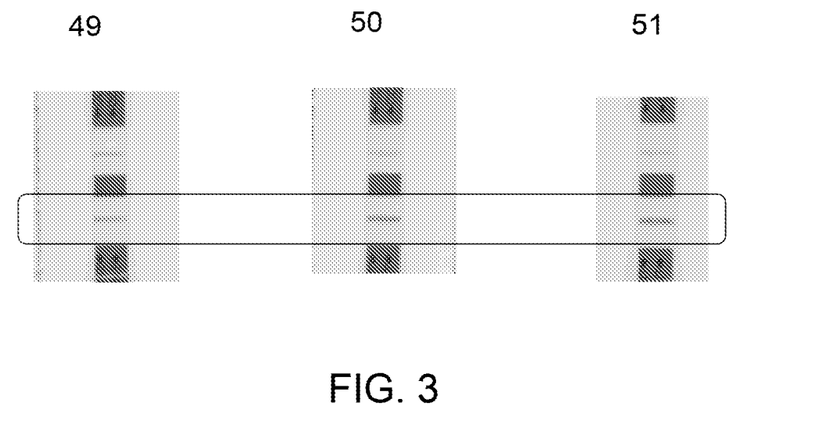
FIG. 3 is an image illustrating different commercially available rapid diagnostic test strips showing presence of TB-LAM in a source biological sample.

As noted above with respect to blocks 22, 24, and 26 of FIG. 1, the source biological sample, the flow through, and the eluate, respectively, may be tested to determine presence or absence of the target biomolecule. Referring now to FIG. 3, three different source biological samples (i), (ii) and (iii) were tested using a commercially available enzyme linked immunosorbent assay (ELISA) kit and/or a commercially available rapid diagnostic test kit. In the illustrated example of FIG. 3, the source biological samples (i)-(iii), such as urine samples, were subjected to commercially available rapid diagnostic test kits 49, 50, and 51 before contacting the source biological samples to respective ion-exchange media. The presence of TB-LAM in the three source biological samples (i)-(iii) was confirmed by the presence of bands in the rapid diagnostic test kits 49, 50 and 51. The rapid diagnostic test kits 49, 50 and 51 showed different concentrations of TB-LAM for the three samples (i)-(iii).

Figure 4:
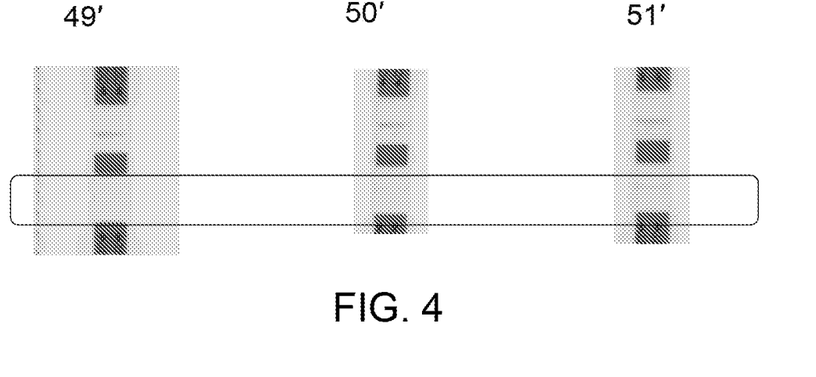

Referring now to FIG. 4, the flow through derived from the three different source biological samples, such as the samples (i)-(iii) used in the example of FIG. 3, were subjected to commercially available rapid diagnostic test strips of the kits, such as 49', 50' and 51'. Absence of any band in the rapid diagnostic test strips 49', 50' and 51' for the flow through derived from the samples (i)-(iii) confirmed the absence of TB-LAM in the flow through of each of the samples. The results shown in FIG. 4 further indicate that the substantial portion of the target biomolecule binds to the ion-exchange medium and therefore the target biomolecule is not present in the flow through.

Figure 5:
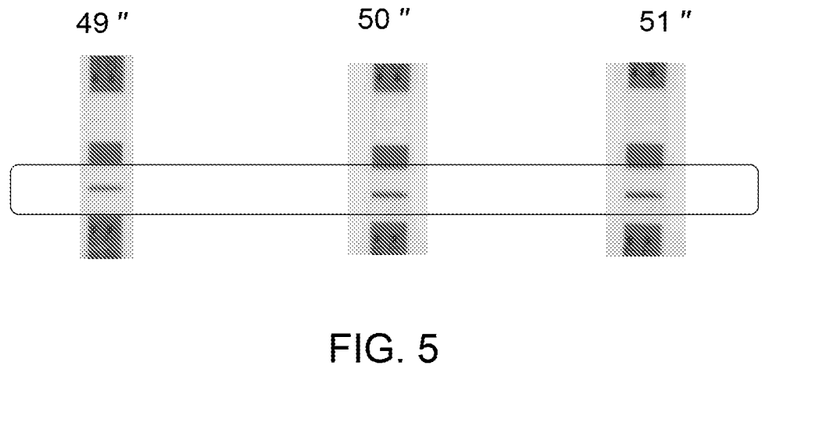
FIG. 5 is an image illustrating different commercially available rapid diagnostic test strips showing presence of TB-LAM in an eluate.

Referring now to FIG. 5, in an example, eluates obtained from the ion-exchange medium for the source biological samples (i)-(iii), were subjected to a commercially available rapid diagnostic test strips of the kits 49", 50" and 51". The presence of TB-LAM in each of the eluate from the three source biological samples (i)-(iii) was confirmed by the presence of bands on the rapid diagnostic test strips, such as 49", 50" and 51" (FIG. 5). The intensity of the bands of TB-LAM on the rapid diagnostic test kits, 49, 50 and 51 of FIG. 3 and strips 49", 50" and 51" of FIG. 5 was higher relative to intensity of the bands obtained using conventional methods. The increase in the intensity of the bands further confirmed generation of higher concentration of TB-LAM in the eluate derived from the three source biological samples (i)-(iii).

FIG. 6 illustrates the results of rapid diagnostic testing of different eluate derived from 5 different source biological samples (iv), (v), (vi), (vii) and (viii), on the rapid diagnostic test strips 52, 54, 56, 58 and 60. The source biological samples (iv)-(viii) were eluted using an ion-exchange medium followed by run on the rapid diagnostic test strips 52, 54, 56, 58, and 60. The concentrations of TB-LAM in the source biological samples (iv)-(viii) were 0, 0.5, 2, 4 and 6 ng/ml (not shown), respectively, wherein the concentrations of the TB-LAM in the eluate derived from the same samples (iv)-(viii) were 0, 7.5, 30, 60 and 90 ng/ml on the rapid diagnostic test strips 52, 54, 56, 58, and 60, respectively. Each of the eluate derived from the samples (iv)-(viii) was concentrated to 15× by contacting the source biological samples to the ion-exchange medium of the concentrator unit. Further, FIG. 7 illustrates the results of rapid diagnostic testing of different source biological samples (ix) and (x) on the test strips 62 (4 ng/ml) and 66 (6 ng/ml), respectively, and their corresponding eluate loaded on the test strips 64 (100 ng/ml) and 68 (150 ng/ml), respectively (as depicted in FIG. 7). Each of the eluate on the test strips 64 and 68 were concentrated to 25× by contacting the source biological samples to the ion-exchange medium 36.

The methods and devices presented herein enable enhanced detection of a target biomolecule in a source biological sample by increasing the concentration of the target biomolecule in the biological sample compared to the concentration of target biomolecule in a sample used for commercially available RDT devices. In some embodiments, a volume of a urine sample generally employed for the device 30, 40 may be in a range from about 2.5 ml to 10 ml. The target biomolecule present in such high volume of the urine sample is more than that is present in a smaller volume of the urine sample. By using the concentrator unit, the target biomolecule is concentrated and eluted form the concentrator unit in 70-100 µL volume. The ability of a device to process larger sample volume by using a concentrator unit indicates that a larger amount of target biomolecule reaches the lateral flow unit while using the device, which results in improving the signal intensity of the device. Advantageously, in the present Application, the device generates ~20× concentrated target biomolecule (or antigen), which allows enhanced intensity signals while using lower volume of the concentrated samples thereby providing improved sensitivity of the point of care (POC) test.

In one or more embodiments, the source biological sample comprises urine, blood, feces, sweat, saliva, mucous, milk, semen, serum, plasma, sputum, tears, tissue, or combinations thereof. For detecting surface polysaccharides (LAM) using different body fluids such as serum, urine or sputum have been investigated, however, none of these body fluids were found to be effective for diagnosing extrapulmonary mycobacterial infections such as those on the rise in HIV-positive subjects. Embodiments of the present method overcome such difficulties by providing enriched mycobacterial antigens TB-LAM in a wide range of sample types from a subject. In some embodiments, the sample types include unprocessed, or undiluted urine sample.

EXAMPLES

Materials: Predictor® ReadyToProcess Adsorber Q+96-well plate column (catalog #17372119) was from GE Healthcare Life Sciences, Pittsburgh, Pa., US. Predictor® ReadyToProcess Adsorber Q+96-well plate column is interchangeably used herein as Q+ membrane column. TB-LAM antigen (from human urine samples) was obtained BioReclamation IVT, Westbury, N.Y. NUNC Maxisorb 96 wells plates (Catalog no 446469-strips or 456537-plates), Capture Antibody (IV-03) of 5 µg/mL; 10% BSA solution (37525), Biotinylated Detection antibody (IV-02b), SA-HRP (streptavidin-horseradish peroxidase) conjugate (Catalog no N100), and 25 mL reservoirs for multichannel pippettor (Catalog no. 8093-11) were purchased from ThermoFisher Scientific, Waltham, Mass., US. Carbonate Coating Buffer (Catalog no C3041-50CAP), PBS-T wash buffer (P3563-10PAK), 0.5 M HCl as a Stop solution (Catalog no 320331-500ML), 1M Tris, pH 8.0 (Catalog no T2694-1L) were obtained from Sigma, St Louis, Mo., US. 10×PBS (Catalog no 17-517Q) was from Lonza, Basel, Switzerland. 3,3',5,5'-Tetramethylbenzidine (TMB) Liquid Substrate System for ELISA (Catalog no ab171523) was from abcam, Cambridge, Mass., US.

The 3,3',5,5'-Tetramethylbenzidine Liquid Substrate System for ELISA is interchangeably used herein as a TMB substrate. Plate covers (plastic cover for short incubations) (Catalog no 353913) were from Falcon®, Corning, N.Y., US and adhesive cover (Catalog no 60941-120) for overnight incubations was from VWR, PA, US.

Example 1: Effect of Dilution of a Source Urine Sample in Concentrating TB-LAM Present in the Source Urine Sample Using an Ion Exchange Medium A urine sample was spiked with TB-LAM to have a final concentration of 24 ng/ml for TB-LAM in the urine sample. The urine sample was diluted to 4× to reduce the conductivity to a range that is optimal for an anion exchange membrane to bind the TB-LAM antigen. 6.2 ml of the diluted urine sample containing 6 ng/ml TB-LAM was applied to a Q+ membrane column, wherein the TB-LAM was captured to the Q+ membrane column (i.e., membrane-bound TB-LAM or captured TB-LAM). The membrane-bound TB-LAM was eluted from the Q+ membrane column using 1.35 M NaCl in 20 mM Tris buffer. 0.1 mL eluate was loaded to an RDT device, wherein the eluate contained TB-LAM at a concentration of 315.1 ng/ml in an elution buffer containing 1.35 M NaCl in 20 mM Tris buffer. The TB-LAM was concentrated to 51.5-fold using the Q+ membrane column. The result yields about 13× increase in concentration using a diluted urine sample (4×) over the undiluted urine sample and commensurate improvement in sensitivity of the RDT.

Example 2: Qualitative Analysis of Urine Sample Containing TB-LAM Before and after Concentrating the Urine Sample Preparation of Q+ membrane columns: Predictor® ReadyToProcess Adsorber Q+96-well plate columns (or Q+ membrane columns) were prepared for binding of TB-LAM antigen from human urine samples by washing each well with 2 mL of acidified buffer solution. After washing the Q+ membrane column, the column was equilibrated with a neutral pH buffer solution (e.g., phosphate buffered saline (PBS)).

Preparation of urine sample containing TB-LAM: TB-LAM antigen was added to a urine sample to attain a TB-LAM concentration of 24 ng/mL. The urine sample was diluted (4× dilution) to generate a diluted urine sample having desired salinity and enable efficient binding to the anion exchange membrane (e.g., ~10 mS/cm). The resulting concentration of TB-LAM antigen was 6 nanogram/mL (ng/mL), which is a level in the typical range for a human TB-infected patient and in the working range of commercially available point-of-care RDTs. The urine was then filtered through a 0.2 um ePTFE filter. The concentration of the TB-LAM used in the following experiments were in a range of 10 picograms/mL to 240 ng/mL.

Concentration of TB-LAM of the source urine sample using Q+ membrane columns: Two 10 mL aliquots and a 25-mL aliquot of diluted urine samples containing 6 ng/mL TB-LAM were contacted to the washed and equilibrated Q+ membrane columns for binding the TB-LAM to the Q+ membrane columns. A fraction of the flow-through from the Q+ membrane column was collected for determining presence or absence of TB-LAM in the flow-through. The rest of the flow through was disposed of after neutralizing the flow through with a bleach. In case of inefficient capture of the TB-LAM by the column, the flow through contains TB-LAM. In case of TB-LAM binding to the Q+ membrane column, the bound TB-LAM was eluted off from the Q+ membrane column using 100l eluate for three times (3×100 uL). The bound TB-LAM was eluted form the column using 1.35 M NaCl in 20 mM Tris buffer. 84.64% of the bound TB-LAM was eluted off the membrane with the first 100 uL of eluate, containing 31.51 ng of TB-LAM. The remaining TB-LAM were eluted in the second (4.69 ng, 12.61%) and third (0.93 ng, 2.75%) aliquots of 100 uL eluate each. The eluate containing TB-LAM was directly applied to a commercially available RDT point-of-care device (or test strip), wherein the eluate contained TB-LAM in an elution buffer of 1.35 M NaCl in 20 mM Tris.

A commercially available RDT point-of-care test was used to qualitatively determine the presence and/or absence of TB-LAM in the source urine sample before applied to the column (FIG. 3), flow-through from the column (FIG. 4), and eluate (FIG. 5) for each sample (N=3). 60 uL of each of the samples, such as source urine sample, flow-through, and eluate was applied to the commercially available RDT per manufacturer's instructions to determine TB-LAM on the test line of the RDT strip. FIG. 3 confirmed the presence of TB-LAM in the source urine sample by the generation of bands of 15 ng/ml, 42.8 ng/ml, and 60 ng/ml in the rapid diagnostic test strips 49, 50 and 51 for samples (i), (ii) and (iii), respectively. FIG. 4 showed absence of any band in the rapid diagnostic test strips 49', 50' and 51' for the flow through derived from samples (i), (ii) and (iii). The results of FIG. 4 confirmed that a substantial portion of TB-LAM of the urine sample was bound to the ion-exchange medium and therefore the TB-LAM was not present in the flow through (FIG. 4, test strips 49', 50' and 51'). FIG. 5 showed the presence of TB-LAM in each of the eluates on the rapid diagnostic test strips, such as 49", 50" and 51" from the samples (i), (ii) and (iii).

The intensity of the bands of TB-LAM on the rapid diagnostic test strips 49, 50 and 51 of FIG. 3 and strips 49", 50" and 51" of FIG. 5 further confirmed generation of higher concentration of TB-LAM in the eluate derived from the source urine samples (i), (ii) and (iii) as compared to the TB-LAM in the source urine samples (i), (ii) and (iii). The source urine sample containing 24 ng/mL TB-LAM (FIG. 3) was passed through the Q+ membrane column. A concentration of the TB-LAM in the eluate collected from the column was determined as 315.1 ng/mL. The concentration of TB-LAM (315.1 ng/mL) in the eluate resulted in an overall concentration factor of about 13×. The concentrated form of TB-LAM ensured generating comparatively stronger response in a commercially available RDT for antigen detection (FIG. 5). The effective volume of the source urine sample containing TB-LAM was reduced from 6.2 mL to 100 uL (eluate), which resulted in concentrating the TB-LAM in the urine sample. A sample with a low TB-LAM titer, which was previously undetectable in RDT would become detectable by the same RDT after concentrating the TB-LAM using this example. FIGS. 6 and 7 also depicted control and test bands for TB-LAM (qualitative representation) in the eluates for the samples (iv)-(viii) (FIG. 6) and samples (ix) and (x) (FIG. 7).

Example 3: Quantitative Analysis of Urine Sample Containing TB-LAM Before and after Concentrating the Urine Sample The source urine sample before applying to the column, and the eluate for different samples (N=2) were quantified by ELISA assay against a standard dilution series of TB-LAM in the solution used at each point of the assay. A quantitative estimation included determination of concentration of TB-LAM in the source urine sample and in eluate by standard ELISA bio-quantification methodology as described below. The eluate containing TB-LAM was directly applied to an ELISA reaction, wherein the eluate contained TB-LAM in an elution buffer of 1.35 M NaCl in 20 mM Tris.

Preparation of reagents for ELISA: Carbonate Coating Buffer was prepared by using contents of 1 capsule material into 100 mL double distilled water (ddH$_2$O). Capture antibody (IV-03) was used as 5 µg/mL concentration. 10% BSA solution was diluted to 1:10 to 1% in 1×PBS to make a Blocking Buffer. Biotinylated antibody was used at a concentration of 0.3 µg/mL in 1×PBS. 1 mg/mL TB-LAM was used for various examples. 10×PBS was diluted in ddH$_2$O in a dilution of 1:10 to form 1×PBS for use as a diluent buffer. For preparing 1×PBS-T wash buffer, content of PBS-T buffer package (as purchased) was dissolved in 1 L ddH$_2$O. The TMB substrate was used as received from manufacturer. 0.5 M HCl was used as a Stop solution. A concentrated (37%) HCl was added to ddH$_2$O in a ratio of 1:24 to prepare a 0.5M HCl. 1M Tris, pH 8.0 was used to normalize pH of urine samples to pH 8.

ELISA Detection Method: Absorbance-based microplate reader, which can read absorbance at 450 nm and preferably at 550 nm was used for ELISA detection. Distilled or deionized water (ddH$_2$O) was used for dilution of the samples or cleaning of tubes or plates. 96-well plate washer (e.g. TECAN) was used for manually washing the plates, if necessary. 12- or 8-channel 200 µL pipettor, 25 mL reservoirs for multichannel pippettor were used for the assays.

Wash Plate procedure: Liquid from each well of the 96-well plate was aspirated and discarded either manually or with an automated plate washer followed by dispensing 300 µL of PBS-T into each well. Dispensing and/or aspiration were repeated for at least two times such that wells had 3×300 µL PBS-T washes. After final aspiration, the assay constituents were added to the wells promptly to prevent drying out the wells.

General Protocol for ELISA: Test samples used for ELISA assay were the TB-LAM spiked urine sample, eluate from the Q+ column for the respective source urine samples. The control sample was an elution buffer (1.35 M NaCl in 20 mM Tris). 100 µL of capture antibody (IV-02) diluted in a carbonate buffer was added to the bottom of each well of a 96-well plate. The 96-well plate was sealed before incubation at 4° C. for overnight. After incubation, 200 µL of blocking buffer was added to each well of the 96-well plate for blocking the antibodies at the bottom of the wells. The 96-well plate was covered and incubated at room temperature for 1 hour. 100 µL of prepared test and control samples were added to the wells of the 96-well plate containing the capture antibodies. The 96-well plate was covered and incubated at room temperature for 1 hour for binding the TB-Lam of the test sample to the capture antibody. 100 µL of diluted detection antibody (IV-02b @ 0.3 pg/mL in 1×PBS) was added to each of the wells for detecting the TB-LAM-bound capture antibody. The plate was covered and incubated at room temperature for 45 minutes for complete binding of the detection antibody to the TB-LAM-bound capture antibody. 100 µL of diluted SA-HRP (Streptavidin-HRP) conjugate was added to each well, wherein the SA-HRP was diluted in a ratio of 1:7,500 in 1×PBS. The SA-HRP conjugate was used for binding to biotinylated detection antibody. The 96-well plate was covered and incubated at room temperature for 30 minutes. A stop solution and a TMB ELISA substrate solution were prepared as per manufacturer's direction. 100 µL of TMB ELISA substrate was added to each well of the 96-well plate without cross contaminating the reservoir. The TMB ELISA substrate generally detects horseradish peroxidase (HRP) activity. Unreacted substrate was typically colorless or generated very light yellow color. When the TMB ELISA substrate system was reacted with peroxidase, a blue-colored soluble reaction product was developed in the wells. The reaction was stopped using a stop solution, producing a soluble yellow reaction product, which was stable for at least 1 hour.

A 96-well plate on a white background was developed on the bench and incubated for about 4-6 minutes, such that a blue color should be clearly visible. Stop solution was added if any well for blank reaction starts forming blue color. 100 µL of stop solution was added to each well in the same order as added to the TMB ELISA substrate, wherein the wells with blue color changed to bright yellow. The plate was evaluated within 30 minutes of stopping the reaction. The absorbance of each well was measured at 450 nm and 550 nm. The absorbance value at 550 nm was subtracted from the absorbance value at 450 nm to correct optical imperfections in the microplate. A curve-fitting statistical software was used to plot a four-parameter logistic curve fit to the standards and then calculated results for the test samples.

Determination of concentration of TB-LAM in urine sample: A concentration of TB-LAM in an eluate collected from a Q+ membrane column was determined quantitatively using an ELISA kit. The concentrations of TB-LAM in the source biological samples (iv), (v), (vi), (vii) and (viii) (referred to herein as (iv)-(viii)) were determined by ELISA as 0, 0.5, 2, 4 and 6 ng/ml (data not shown). The concentrations of TB-LAM in the corresponding eluates were determined by ELISA as 0, 7.5, 30, 60 and 90 ng/ml. The same eluates of samples (iv)-(viii) were run on the rapid diagnostic test strips 52, 54, 56, 58, and 60, respectively (FIG. 6). TB-LAM in the eluates derived from the samples (iv)-(viii) were concentrated to 15× by contacting the source urine samples to the Q+ membrane column of the concentrator unit.

Further, the concentrations of TB-LAM were determined as 4 and 6 ng/ml in source urine samples (ix) and (x) respectively and 100 and 150 ng/ml in the eluates corresponding to the same samples (ix) and (x), respectively. The source urine samples (ix) and (x) and corresponding eluates were also applied to the rapid diagnostic testing strips 62, 64, 66, and 68, as shown in FIG. 7. Each of the eluate on the test strips 64 (100 ng/ml) and 68 (150 ng/ml) were concentrated to 25× by contacting the source biological samples 62 (4 ng/ml) and 66 (6 ng/ml) to the ion-exchange medium.

While only certain features of the invention have been illustrated and described herein, many modifications and changes will occur to those skilled in the art. It is, therefore, to be understood that the appended embodiments are intended to cover all such modifications and changes as fall within the scope of the invention.

The invention claimed is:

1. A method for rapid diagnostic testing of a source biological sample comprising tuberculosis-lipoarabinomannan (TB-LAM), comprising:
concentrating the TB-LAM by:
diluting the source biological sample by at least 2× to form a diluted biological sample;
contacting the diluted biological sample to an anion-exchange medium to capture the TB-LAM of the diluted biological sample;

capturing the TB-LAM of the diluted biological sample by the anion-exchange medium; and eluting captured-TB-LAM from the anion-exchange medium as a concentrated form of TB-LAM in an eluate under a salt concentration of at least 1M, wherein a concentration of the TB-LAM in the eluate is in a range from about 2x to 25x compared to a concentration of the TB-LAM in the diluted biological sample; and loading the eluate comprising the concentrated form of the TB-LAM to a rapid diagnostic testing device comprising a TB-LAM-specific antibody for binding the concentrated form of the TB-LAM, wherein the eluate is loaded without any dilution, and wherein the TB-LAM binds to the TB-LAM-specific antibody under the salt concentration of at least 1M.

2. The method of claim 1, wherein the TB-LAM-specific antibody is a reporter-linked TB-LAM-specific antibody.

3. The method of claim 2, further comprising generating a signal on binding of the TB-LAM to the TB-LAM-specific antibody in case of exceeding a pre-determined threshold value for a concentration of the TB-LAM.

4. The method of claim 1, wherein the captured-TB-LAM binds to the TB-LAM-specific antibody under the salt concentration in a range from about 1M to 2M.

5. The method of claim 1, wherein the captured-TB-LAM binds to the TB-LAM-specific antibody under the salt concentration of about 1.3M.

6. The method of claim 1 further comprising diluting the source biological sample by 4x to form the diluted biological sample.

7. The method of claim 1, wherein the rapid diagnostic testing device comprises a lateral flow assay (LFA) device, an enzyme linked immuno-sorbent assay (ELISA) device, or a combination thereof.

8. The method of claim 7, wherein the rapid diagnostic testing device comprises a lateral flow assay (LFA) device.

9. The method of claim 1, wherein the source biological sample comprises urine, blood, feces, sweat, saliva, mucous, milk, semen, serum, plasma, sputum, tears, tissue, or combinations thereof.

10. The method of claim 9, wherein the source biological sample is urine.

11. A device, comprising: a dilutor unit configured to dilute a biological sample; a concentrator unit configured to receive diluted biological sample from the dilutor unit via an inlet coupling the dilutor unit to the concentrator unit, the concentrator unit comprising an anion exchange medium to concentrate an antigen from the diluted biological sample and generate a concentrated form of the antigen; and an immune-based assay unit comprising an antibody to bind the concentrated form of the antigen received from the concentrator unit, wherein the concentrator unit is operatively coupled to the immune-based assay unit via an outlet to allow loading of the concentrated form of the antigen from the concentrator unit to a sample receiving zone of the immune-based assay unit.

12. The device of claim 11, wherein the antigen is TB-LAM.

13. The device of claim 12, wherein the immune-based assay unit comprises rapid diagnostic testing device, enzyme linked immune sorbent assay (ELISA), or lateral flow assay.

14. A method for rapid diagnostic testing of a source biological sample comprising tuberculosis-lipoarabinomannan (TB-LAM), comprising:

concentrating the TB-LAM by:
diluting the source biological sample by at least 2x to form a diluted biological sample;

contacting the diluted biological sample to an anion-exchange medium to capture the TB-LAM of the diluted biological sample;

capturing the TB-LAM of the diluted biological sample by the anion- exchange medium; and eluting the captured-TB-LAM from the anion-exchange medium as a concentrated form of TB-LAM in an eluate under a salt concentration greater than 150 mM, wherein a concentration of the TB-LAM in the eluate is in a range from about 2x to 25x compared to a concentration of the TB-LAM in the diluted biological sample; and loading the eluate comprising the concentrated form of the TB-LAM to a rapid diagnostic testing device comprising a TB-LAM-specific antibody for binding the concentrated form of the TB-LAM, wherein the eluate is loaded without any dilution, and wherein the TB-LAM binds to the TB-LAM-specific antibody under the salt concentration greater than 150 mM.

15. The method of claim 14, wherein the TB-LAM-specific antibody is a reporter-linked TB-LAM-specific antibody.

16. The method of claim 15, further comprising generating a signal on binding of the TB-LAM to the TB-LAM-specific antibody in case of exceeding a pre-determined threshold value for a concentration of the TB-LAM.

17. The method of claim 14 further comprising diluting the source biological sample by 4x to form the diluted biological sample.

18. The method of claim 14, wherein the source biological sample comprises urine, blood, feces, sweat, saliva, mucous, milk, semen, serum, plasma, sputum, tears, tissue, or combinations thereof.

* * * * *